(12) United States Patent
Yamashita et al.

(10) Patent No.: US 7,671,220 B2
(45) Date of Patent: Mar. 2, 2010

(54) PROCESSES FOR THE 3,3-DIALKYLATION OF 4-CHROMANONES

(75) Inventors: Ayako Yamashita, Englewood, NJ (US);
Emily B. Norton, Nanuet, NY (US);
Jaechul Shim, Oakland, NJ (US); Cilien S. Hanna, Garnerville, NY (US)

(73) Assignee: Wyeth, Madison, NJ (US)

( * ) Notice: Subject to any disclaimer, the term of this patent is extended or adjusted under 35 U.S.C. 154(b) by 956 days.

(21) Appl. No.: 11/354,531

(22) Filed: Feb. 15, 2006

(65) Prior Publication Data
US 2006/0183924 A1 Aug. 17, 2006

Related U.S. Application Data

(60) Provisional application No. 60/653,599, filed on Feb. 16, 2005.

(51) Int. Cl.
*C07D 311/00* (2006.01)
(52) U.S. Cl. .................. 549/399; 549/400; 549/401
(58) Field of Classification Search .............. 549/401, 549/399, 400
See application file for complete search history.

(56) References Cited

U.S. PATENT DOCUMENTS 5,470,872 A * 11/1995 Buckle et al. .............. 514/456
6,110,956 A   8/2000 Mewshaw et al.

OTHER PUBLICATIONS

Klemm et al, Jol. Org. Chem., pp. 1480-1488; DOI: 10.1021/jo01268a036.*
Hattersley et al., "Some alkylation and gringnard reactions with 1-tetralones and related compounds," *J Chem Society* (1969) pp. 217-222.
Jones et al., *The Chemistry of Fungi. Part II. Derivatives of 3 : 4-Dimethoxyphenol*, University of Liverpool (1948) 121:562-569.
Lachapelle et al., "Conformational analysis of 3-substituted-2,3,4,5-tetrahydro-1-benzoxepin by $^1$H and $^{13}$C nuclear magnetic resonance," *Can J Chem* (1987) 65:2575-2594.
Miller et al., "The metal-promoted fries rearrangement," *J Org Chem* (1987) 52:322-323.
Padfield et al., "The action of sodium ethoxide on chroman-4-ones," *J Chem Soc.* (1950) 2272-2277.
Zimmerman et al., "The bicycle rearrangement. Relationship to the di-π-methane rearrangement and control by bifunnel distortion. Mechanistic and exploratory organic phytochemistry[1,2]," *J of the Am Chem Soc* (1980) 102(10):3538-3548.
Akuamoah et al., "Studies of chromenes. Part 11.[1] 3-substitution of 7-methoxy-2,2-dimethylchroman-4-one without ring opening via 3-bromination," *J Chem Soc Perkin Trans* (1995) 197-201.
Anatasis et al., "Studies of chromenes. Part 7.[1] product stabilization in condensations with 7-methoxy-2,2-dimethylchroman-4-one," *J Chem Research (M)* (1989) pp. 429-445.

Anastasis et al., "Studies of chromens. Part 2. Synthesis of 7-methoxy-2,2-dimethylchromen-3-carboxylic acid," *J Chem Soc Perkin Trans I* (1983) 197-200.
Bachi et al., "Homolytic-cyclization of senenil esters. Synthesis of chromanones," *Heterocycles* (1989) 28(2):583-588.
Barlocco et al., "Hydroxymethylation of 2-hydroxypropiophenones in aqueous medium: synthesis of 3-hydroxymethyl-3-methyl-4-chromanones and their conversion to 3-methyl-4-chromanone-3-acetic acids," *Synthesis* (1985) 876-878.
Brown et al., "Studies of chromences. Part 6.[1] 3-hydroxymethyl- and 3-formylprecocenes: potential precursors of other 3-substituted precocenes," *J Chem Research (M)* (1988) pp. 1634-1650.
Crich et al., "Generation and cyclization of acyl radicals from thiol esters under nonreducing, tin-free conditions," *J Org Chem* (1997) 62:5982-5988.
Crich et al., "Generation of acyl radicals from thiolesters by intramolecular homolytic substitution at sulfur," *J Org Chem* (1996) 61:3566-3570.
Crich et al., "Carbonyl radical cyclizations: preparation of some heterocyclic ketones," *Heterocycles* (1989) 28(1):67-70.
Davis et al., "Enantioselective synthesis of tertiary alpha-hydroxy carbonyl compounds using ((8,8-dichlorocamphoryl)sulfonyl)oxaziridine," *J Org Chem* (1990) 55:3715-3717.
Green et al., *Protective Groups in Organic Synthesis*, 2$^{nd}$ ed., Wiley & Sons (1991).
Ahluwalia et al., "Synthesis of 2-hydroxy-2,3-dihydrochromones and structures of Claisen condensation products of phloracetophenone dimethyl ether and .beta.-orcacetophenone monomethyl ether with ethyl formate," *Indian Journal of Chemistry, Section B* (1977) 15B(4):331-334.
Anastasis et al., "Studies of chromenes. Part 7. Product stabilization in condensations with 7-methoxy-2,2-dimethylchroman-4-one," *J of Chemical Research* (1989) (2):36-37.
Cascaval "2-Hydroxyketones; XII. A simple synthesis of 3,3,6,8-tetrasubstituted 4-chromanones," *Synthesis* (1983) (7):579-580.
Cid et al., "Selective alpha-monoallylation of phenyl ketones and benzocycloalkanones under microwave irradiation," *Tetrahedron Letters* (2004) 45(6):1133-1136.
Finaru et al., "Synthesis of 4-chromanone-type Mannich-Werner bases," *Journal de la Societe Algerienne de Chimie* (1999) 9(1):85-90.
Klemm et al., "Alumina-catalyzed rreactions of hydroxyarenes and hydroaromatic ketones. I. Reactions of 1-naphthol with methanol," *Journal of Organic Chemistry* (1968) 33(4):1480-1488.
Poonam et al., "Synthesis and lipase-mediated steroselective deacetylation of (+/-)-3-acetoxymethyl-3-alkyl-7-methoxychroman-4-ones," *Tetrahedron* (2001) 57(34):7395-7402.

(Continued)

*Primary Examiner*—Janet L. Andres
*Assistant Examiner*—Raymond Covington
(74) *Attorney, Agent, or Firm*—Pepper Hamilton LLP

(57) ABSTRACT

The present invention relates to methods for the preparation of 3,3-dialky 4-chromanones, and particularly to the preparation of 6-fluoro-3,3-dimethyl-2,3-dihydro-4H-chromen-4-one and 3,3-dimethyl-2,3-dihydro-4H-chromen-4-one. In some embodiments, the processes include reaction of a 4-chromanone compound with an alkyl halide in the presence of a metal alkoxide at low temperature.

77 Claims, No Drawings

OTHER PUBLICATIONS

Trikha et al., "Candida rugosa lipase-mediated enantioselective acetylation studies on (.+-.)-3-arylmethyl-3-hydroxymethyl-2,3-dihydro-1-benzopyran-4(H)- ones," *Indian Journal of Chemistry, Section B* (2005) 44B(2):356-365.

Yamashita et al., "Synthesis of 3,3-dimethyl-4-chromanones: improved procedures without ring opening," *Synthetic Communications* (2005) 36(4):465-472.

Electronic Table of Contents, Synthetic Communications, 36(4), 2006, pp. 465-472. (http://www.informaworld.com/smpp/title~content=g741547007~db=all).

Electronic Graphical Abstracts, Synthetic Communications, 36(4), 2006, pp. 465-472. (http://pdfserve.informaworld.com/901772_741545486.pdf).

Electronic Abstract and article order page, Synthetic Communications, 36(4), 2006, pp. 465-472. (http://www.informaworld.com/smpp/content~content=a741545497~db=all~order=page).

Electronic Listing of Synthetic Communications publications from 2005-2006, indicating the vol. 36 corresponds to the 2006 calendar year. (http://www.informaworld.com/smpp/title~content=t713597304~db=all).

* cited by examiner

PROCESSES FOR THE 3,3-DIALKYLATION OF 4-CHROMANONES

CROSS REFERENCE TO RELATED APPLICATION

The present invention claims benefit of priority to U.S. provisional application, Ser. No. 60/653,599 filed Feb. 16, 2005, which is incorporated herein by reference in its entirety.

FIELD OF THE INVENTION

The present invention relates to methods for the preparation of 3,3-dialky 4-chromanones, and particularly to the preparation of 6-fluoro-3,3-dimethyl-2,3-dihydro-4H-chromen-4-one and 3,3-dimethyl-2,3-dihydro-4H-chromen-4-one.

BACKGROUND OF THE INVENTION 3,3-Dialkylated 4-chromanones, and particularly 6-fluoro-3,3-dimethyl-4-chromanone and 3,3-dimethyl-4-chromanone, are key intermediates in the preparation of agents that are useful for the treatment of depression [See U.S. Pat. No. 6,110,956, incorporated herein by reference].

The synthesis of 3,3-dialkylated 4-chromanones by direct alkylation is rendered difficult by the tendency to undergo ring opening to a phenolate anion under basic conditions [See Brown, P. E. and Islam, Q., *J. Chem. Research (M)* (1988) 1634; Anastasis, P. et al., *J. Chem. Research (M)* (1989) 429]. Even with these established methods of alkylation, mono alkylation usually dominates, and a second alkylation often either results in low yields or in ring opening [See Anastasis, P. and Brown, P. E., *J. Chem. Soc. Perkin Trans. I* (1983) 197]. Given the importance of 3,3-dialkylated 4-chromanones, and particularly 6-fluoro-3,3-dimethyl-4-chromanone and 3,3-dimethyl-4-chromanone, it can be seen that improved synthetic routes for their preparation are needed. This invention is directed to these, as well as other, important ends.

SUMMARY OF THE INVENTION

In one aspect, the present invention provides improved synthetic processes for the 3,3-dialkylation of 4-chromanones. In accordance with some embodiments of the invention, an optionally substituted 4-chromanone compound having hydrogen atoms at the 3-position thereof is reacted with an alkyl halide or alkenyl halide in the presence of a metal alkoxide for a time and under conditions effective to form a 3,3-dialkylated compound in high yield. In some embodiments, the reaction is performed at a low temperature, for example, less than about 0° C., preferably, less than about −20° C., less than about −40° C., less than about −60° C., less than about −70° C., or at a temperature that is about −78° C. or lower.

DETAILED DESCRIPTION OF THE INVENTION

In some embodiments, the invention provides processes for the preparation of 4-chromanone compounds having the Formula I:

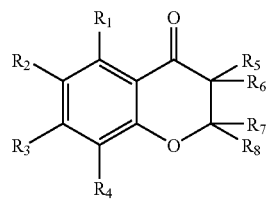

wherein:

$R_1$, $R_2$, $R_3$, $R_4$, $R_7$ and $R_8$ are each, independently, selected from the group consisting of H, halogen, $C_{1-6}$ alkyl, $C_{1-6}$ alkoxy, $C_{1-3}$ perhaloalkyl and $C_{1-6}$ perhaloalkoxy;

wherein the $C_{1-6}$ alkyl and the $C_{1-6}$ alkoxy are each optionally substituted with up to five substituents, independently, selected from the group consisting of halogen, phenyl, aryl, tertiary amines, optionally protected hydroxyl and optionally protected amino;

$R_5$ and $R_6$ are each independently $C_{1-12}$ alkyl or $C_{3-12}$ alkenyl, each of which is optionally substituted with up to five substituents, independently, selected from the group consisting of halogen, phenyl, aryl, tertiary amines, optionally protected hydroxyl and optionally protected amino;

comprising:

a) reacting a compound of Formula II:

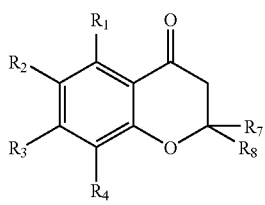

with a $C_{1-12}$ alkyl halide or $C_{3-12}$ alkenyl, in the presence of a metal alkoxide, for a time and under conditions effective to form the compound of Formula I.

While not wishing to be bound by any particular theory, it is believed that the reaction of the compound of Formula II with an alkyl halide in the presence of the base provides two products—the 3,3-dialkylated product and a dimerization product, as shown below for the reaction of 2,3-dihydro-4H-chromen-4-one and 6-fluoro-2,3-dihydro-4H-chromen-4-one with methyl iodide in the presence of potassium tertiary butoxide:

Scheme 1

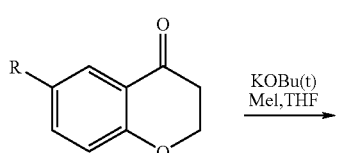

R = F  A
R = H  B

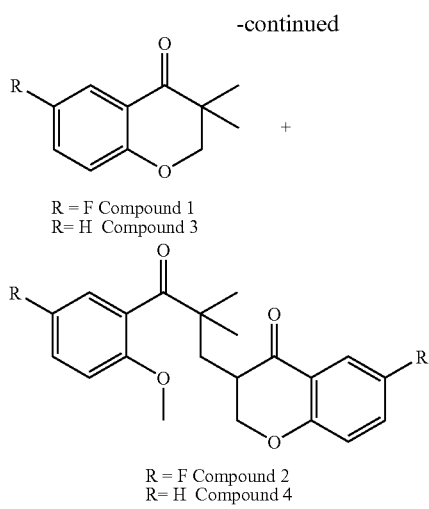

R = F Compound 1
R = H Compound 3

R = F Compound 2
R = H Compound 4

It has been found in accordance with the present invention that ring opening of the 4-chromanone to a phenolate anion under the basic reaction conditions, and hence the production of dimerization products, can be minimized by performing the reaction of the 4-chromanone and the $C_{1-12}$ alkyl halide in the presence of the metal alkoxide at a low temperature, i.e., a temperature that is less than about 0° C., preferably, less than about −20° C., less than about −40° C., less than about −60° C., less than about −70° C., or at a temperature that is about −78° C. or lower.

In some embodiments, the $C_{1-12}$ alkyl halide is a $C_{1-12}$ alkyl iodide, for example, a $C_{1-3}$ alkyl iodide, preferably, methyl iodide. In some embodiments, the $C_{3-12}$ alkenyl is an alkenyl halide such as alkenyl iodide.

In some embodiments, the processes of the invention are used to prepare compounds of Formula I wherein $R_2$ is hydrogen or halogen, preferably, where $R_2$ is hydrogen or fluorine. In some embodiments, the processes of the invention are used to prepare compounds of Formula I wherein $R_2$ is hydrogen or halogen, and $R_1$, $R_3$, $R_4$, $R_7$ and $R_8$ are each hydrogen. In some such embodiments, $R_5$ and $R_6$ are each methyl. In some embodiments, the processes of the invention are used to prepare 3,3-dimethyl-2,3-dihydro-4H-chromen-4-one and 6-fluoro-3,3-dimethyl-2,3-dihydro-4H-chromen-4-one.

Suitable bases for use in the reaction of compounds of Formula II and the $C_{1-12}$ alkyl halide or $C_{3-12}$ alkenyl halide according to the processes of the invention include, e.g., metal alkoxides such as sodium ethoxide, potassium ethoxide, sodium t-butoxide, potassium t-butoxide, and the like. In some embodiments, the base is tertiary butoxides, for example, potassium t-butoxide.

The reactions of the processes described herein can be carried out in suitable solvents that can be readily selected by one of skill in the art of organic synthesis. Suitable solvents are preferably, substantially, nonreactive with the starting materials (reactants), the intermediates, or the products at the temperatures at which the reactions are carried out. As the reaction of the 4-chromanone, the alkyl halide and metal alkoxide are preferably, performed at low temperature, the solvent should be one that will be a liquid at those temperatures. In some embodiments, the solvent is an ether, for example, a cyclic ether such as tetrahydrofurazan.

Generally, the alkyl halide or alkenyl hailde and the metal alkoxide are present in the reaction mixture in molar excess relative to the 4-chromanone. In some embodiments, the alkyl halide or alkenyl hailde and the metal alkoxide are present in the reaction mixture in greater than about one molar excess relative to the 4-chromanone (e.g., a compound of Formula II).

In some embodiments, the molar ratio of alkyl halide or alkenyl hailde to compound of Formula II is from about 2 to about 20, or from about 2 to about 10, or from about 2 to about 8, or from about 4 to about 7, or about 5 to about 6.

In some embodiments, the molar ratio of metal alkoxide to 4-chromanone is from about 2 to about 10, or from about 3 to about 7, or from about 4 to about 6.

While the order of the addition of the reagents of the reaction can be varied, it is generally preferred to initiate the reaction by combining a solution containing the 4-chromanone and the alkyl halide or alkenyl hailde with either the metal alkoxide alone or the metal alkoxide in a solvent. For example, to a solution containing the 4-chromanone starting material (e.g., a compound of Formula II) and the alkyl halide or alkenyl hailde, preferably, in a solvent, the metal alkoxide can be added to this solution either as a solid in portions, or as a solution in a solvent. Alternatively, a solution containing the metal alkoxide in a solvent can be prepared, and a solution containing the 4-chromanone starting material (e.g., a compound of Formula II) and the alkyl halide or alkenyl hailde, preferably, in a solvent, can be added thereto. In some embodiments, the solvent for the solution of the metal alkoxide and the solvent for the solution of the 4-chromanone and the alkyl halide or alkenyl hailde are the same.

Preferably, the temperature of the reaction mixture is maintained low, as discussed above, during the combination of the 4-chromanone, alkyl halide or alkenyl hailde and metal alkoxide. However, after the combination of the reactants, depending on the reactivity of the particular 4-chromanone and alkyl halide or alkenyl hailde, it may be advantageous to heat the reaction for an appropriate time and at an appropriate temperature to maximize product yield. In some cases, it can be advantageous to allow the reaction mixture to reach ambient temperature, or to heat the reaction mixture at various temperatures for various periods of time in order to maximize product yield.

For example, in some embodiments, after combination of the 4-chromanone, alkyl halide or alkenyl hailde and metal alkoxide at low temperature, the reaction mixture is allowed to reach ambient temperature, and the product is collected. In other embodiments, the reaction mixture is heated above room temperature, for example, between about 40° C. and about 80° C., or between about 50° C. and about 70° C., or at about 60° C., or at the reflux temperature of the solvent. Such heating, if required, can be performed for any suitable time, for example, from about one to about 6 hours, or from about two to about five hours, or about four hours. In some embodiments, it may be beneficial to maintain the reaction mixture at ambient temperature for a suitable period of time, followed by heating for an additional period of time, as described above, and then again maintaining the reaction mixture at ambient temperature for an additional period of time. For example, in some embodiments, after combination of the 4-chromanone, alkyl halide or alkenyl hailde and metal alkoxide at low temperature, the reaction mixture is warmed to room temperature, and then heated as described above, for example, at about 60° C. for four hours. The reaction mixture is then cooled to ambient temperature and stirred for an additional period of time, for example, from one to about 20 hours, preferably, about fifteen hours, and then collected.

The product of the reaction may be isolated by various techniques known in the art. For example, in some cases it might be preferable to isolate the reaction product by extraction with an appropriate solvent or mixture of solvents, for example, diethyl ether, and subsequent chromatography. Alternatively, it might be preferable in some cases to directly collect the product.

In some embodiments, the product can be further purified by recrystallization. The recrystallization can be performed with a solvent or a mixture of solvents. In some embodiments, the product can be further purified by chromatography, for example, on silica gel. Suitable elution solvents include halogenated hydrocarbons, for example, methylene chloride. Other suitable solvents will be apparent to those of skill in the art.

The isolated product may be further purified by washing one or more times with an appropriate solvent or mixture of solvents.

The processes of the invention provide product compounds of Formula I in yields of greater than about 50%, about 60%, about 70%, about 80%, about 90%, about 95%, about 96%, about 97%, about 98%, about 99%, or substantially about 100%.

In addition, the processes of the invention provide products that contain reduced amounts of dimerization products of Formula III. In some embodiments, the processes of the invention provide products of Formula I that contain less than about 50% of such dimeric products, less than about 25% of such dimeric products, less than about 10% of such dimeric products, less than about 5% of such dimeric products, less than about 3% of such dimeric products, less than about 1% of such dimeric products, or that are substantially free of such dimeric products.

The term "about," as used herein in conjunction with a value is meant to refer to ten percent, plus or minus (+/−), the value with which it is used.

As used herein, the term "alkyl" or "alkylene" is meant to refer to a saturated hydrocarbon group that is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. An alkenyl group can contain from 3 to about 20, from 3 to about 12, from 3 to about 10, from 3 to about 8, from 3 to about 6, from 3 to about 4, or about 3 carbon atoms. Example alkenyl groups include ethenyl, propenyl, butenyl, pentenyl, hexenyl, butadienyl, pentadienyl, hexadienyl, and the like.

As used herein, "halo" or "halogen" refers to fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, the term "aryl" refers to aromatic carbocyclic groups including monocyclic or polycyclic aromatic hydrocarbons such as, for example, phenyl, 1-naphthyl, 2-naphthyl anthracenyl, phenanthrenyl, and the like. In some embodiments, aryl groups have from 6 to about 20 carbon atoms.

The term "tertiary amines", when used in the definitions of the substituent groups of Formulas I, II and III herein, means a moiety of formula —$R_9$—$N(R_{10})(R_{11})$, wherein each of $R_9$, $R_{10}$ and $R_{11}$, is independently $C_{1-12}$ alkyl or $C_{7-24}$ arylalkyl.

The term arylalkyl is intended to mean a group of formula -alkyl-aryl, for example, a benzyl or naphthylmethyl group.

The term "amino" is intended to denote —$NH_2$.

As used herein, the term "reacting" refers to the bringing together of designated chemical reactants such that a chemical transformation takes place generating a compound different from any initially introduced into the system. Reacting can take place in the presence or absence of solvent.

Preparation of compounds can involve the protection and deprotection of various chemical groups. Specific examples include hydroxyl and amino groups. For example, in the preparation of compounds of Formula I having hydroxyl substituents, a suitable protecting group can be employed during synthesis, and subsequently removed. The need for protection and deprotection, and the selection of appropriate protecting groups can be readily determined by one skilled in the art. The chemistry of protecting groups can be found, for example, in Greene, et al., *Protective Groups in Organic Synthesis,* 2d. ed., Wiley & Sons, 1991, which is incorporated herein by reference in its entirety.

At various places in the present specification substituents of compounds of the invention are disclosed in groups or in ranges. It is specifically intended that the invention include each and every individual sub-combination of the members of such groups and ranges. For example, the term "$C_{1-6}$ alkyl" is specifically intended to individually disclose methyl, ethyl, $C_3$ alkyl, $C_4$ alkyl, $C_5$ alkyl and $C_6$ alkyl.

The compounds of the present invention can contain an asymmetric atom, and some of the compounds can contain one or more asymmetric atoms or centers, which can thus give rise to optical isomers (enantiomers) and diastereomers. The present invention includes such optical isomers (enantiomers) and diastereomers (geometric isomers), as well as, the racemic and resolved, enantiomerically pure R and S stereoisomers, as well as, other mixtures of the R and S stereoisomers, and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The processes described herein can be monitored according to any suitable process known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography (TLC). Such techniques can be used to detect the disappearance of starting material (e.g., compound of Formula II), or detect the appearance of 3,3-dialkylated product, or both.

In some embodiments, the techniques above can be used to assess the purity of the reaction mixture, or of a solution containing the product of the reaction, by detecting any dimeric product formed. Thus, the dimeric compounds of Formula III are useful as, for example, impurity standards in the qualitative and quantitative analyses of compounds of Formula I.

Accordingly, in a further aspect, the present invention provides processes for the preparation of a compound of Formula III:

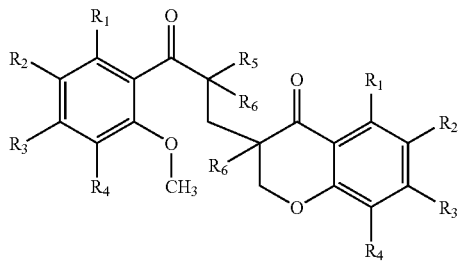

wherein:

R$_1$, R$_2$, R$_3$ and R$_4$ are each, independently, selected from the group consisting of H, halogen, C$_{1-6}$ alkyl, C$_{1-6}$ alkoxy, C$_{1-3}$ perhaloalkyl and C$_{1-6}$ perhaloalkoxy;

wherein said C$_{1-6}$ alkyl and said C$_{1-6}$ alkoxy are each optionally substituted with up to five substituents, independently, selected from the group consisting of halogen, phenyl, aryl, tertiary amines, optionally protected hydroxyl and optionally protected amino;

R$_5$ and R$_6$ are each independently C$_{1-12}$ alkyl or C$_{1-12}$ alkenyl, each of which is optionally substituted with up to five substituents, independently, selected from the group consisting of halogen, phenyl, aryl, tertiary amines, optionally protected hydroxyl and optionally protected amino;

comprising:

a) reacting a compound of Formula II:

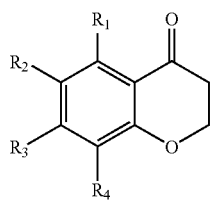

with a C$_{1-12}$ alkyl halide or C$_{3-12}$ alkenyl halide in the presence of a metal alkoxide for a time and under conditions effective to form the compound of Formula III.

In some embodiments, the reaction of the compound of Formula II and the C$_{1-12}$ alkyl halide or C$_{3-12}$ alkenyl halide in the presence of the metal alkoxide is performed at a temperature that is greater than about −10° C., or about −0° C. or greater, or about 10° C. or greater, or about 20° C. or greater.

In some embodiments, the C$_{1-12}$ alkyl halide is a C$_{3-12}$ alkyl iodide, for example, methyl iodide. In some embodiments, the C$_{1-12}$ alkenyl halide is a C$_{3-12}$ alkenyl iodide, for example, alkenyl iodide In some embodiments, the metal alkoxide is a tertiary butoxide, for example, potassium tert-butoxide.

In some embodiments, the compound of Formula II and the C$_{1-12}$ alkyl halide or C$_{3-12}$ alkenyl halide are reacted in the presence of potassium tert-butoxide at a temperature that is about 0° C. or greater.

In some embodiments, R$_2$ is H or halogen. In some further embodiments, R$_2$ is H or halogen, and R$_1$, R$_3$ and R$_4$ are each H. In some further embodiments, R$_2$ is H or halogen, R$_1$, R$_3$ and R$_4$ are each H, and R$_5$ and R$_6$ are each methyl.

In some embodiments, the C$_{3-12}$ alkyl halide is methyl iodide, the metal alkoxide is potassium tert-butoxide, R$_2$ is H or halogen, and R$_1$, R$_3$ and R$_4$ are each H. In some such embodiments, the compound of Formula II and the methyl iodide are reacted in the presence of potassium tert-butoxide at a temperature that is about −0° C. or greater, or about 10° C. or greater, or about 20° C. or greater. In some embodiments, the C$_{3-12}$ alkenyl halide is alkenyl iodide, the metal alkoxide is potassium tert-butoxide, R$_2$ is H or halogen, and R$_1$, R$_3$ and R$_4$ are each H. In some such embodiments, the compound of Formula II and the methyl iodide are reacted in the presence of potassium tert-butoxide at a temperature that is about −0° C. or greater, or about 10° C. or greater, or about 20° C. or greater.

In some embodiments, the reaction is performed in a solvent, preferably, tetrahydrofuran. In some embodiments, the molar ratio of C$_{1-12}$ alkyl halide or C$_{3-12}$ alkenyl halide to compound of Formula II is from about 2 to about 20, or from about 2 to about 10, or from about 2 to about 8, or from about 4 to about 7, or from about 5 to about 6.

In some embodiments, the molar ratio of metal alkoxide to compound of Formula II is from about 2 to about 10, or from about 3 to about 7.

In some embodiments for the preparation of a compound having the Formula I, the process includes the reaction of the compound of Formula II and an C$_{1-12}$ alkyl halide or C$_{3-12}$ alkenyl halide in the presence of the metal alkoxide at a temperature that is about −78° C. or lower, where the C$_{1-12}$ alkyl halide is methyl iodide or the C$_{3-12}$ alkenyl halide is alkenyl iodide, the metal alkoxide is a potassium tert-butoxide, R$_2$ is H or fluorine, R$_1$, R$_3$, R$_4$, R$_7$ and R$_8$ are each H, and R$_5$ and R$_6$ are each methyl. In some such embodiments, the solvent is tetrahydrofuran.

In some embodiments for the preparation of a compound of Formula III, the process includes the reaction of the compound of Formula II and an C$_{1-12}$ alkyl halide or C$_{3-12}$ alkenyl halide in the presence of the metal alkoxide at a temperature that is about 0° C. or greater, where the C$_{1-12}$ alkyl halide is methyl iodide or the C$_{3-12}$ alkenyl halide is alkenyl iodide, the metal alkoxide is a potassium tert-butoxide, R$_2$ is H or fluorine, R$_1$, R$_3$, R$_4$, R$_7$ and R$_8$ are each H, and R$_5$ and R$_6$ are each methyl. Some such embodiments, the solvent is tetrahydrofuran.

The reactions of the processes described herein can be carried out in air or under an inert atmosphere. Typically, reactions containing reagents or products that are substantially reactive with air can be carried out using air-sensitive synthetic techniques that are well known to the skilled artisan.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

The processes of this invention are suitable for the preparation of compounds of Formula I on any convenient scale, for example, greater than about 0.01 mg, 0.10 mg, 1 mg, 10 mg, 100 mg, 1 g, 10 g, 100 g, 1 kg, 10 kg or more. The processes are particularly advantageous for large scale (e.g., greater than about ten grams) preparation of compounds of 3,3-dialkylated-4-chromanones.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

EXAMPLES

Example 1

Reaction of 6-fluoro-2,3-dihydro-4H-chromen-4-one with Methyl Iodide in the Presence of Potassium Tertiary Butoxide at 0° C.

Preparation of 6-fluoro-3,3-dimethyl-2,3-dihydro-4H-chromen-4-one, Compound 1, and 6-fluoro-3-[3-(5-fluoro-2-methoxyphenyl)-2,2-dimethyl-3-oxopropyl]-3-methyl-2,3-dihydro-4H-chromen-4-one, Compound 2

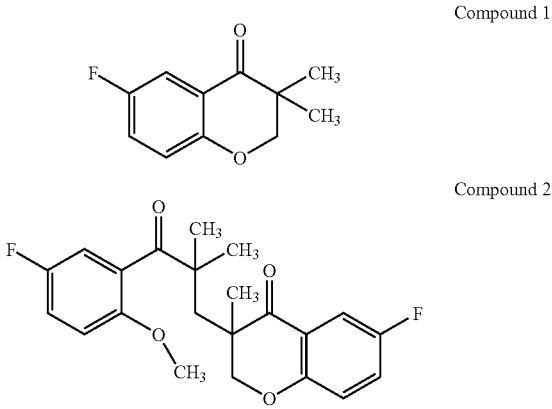

A solution of 6-fluoro-2,3-dihydro-4H-chromen-4-one (60 grams, 0.36 mole, purchased from Aldrich Co., Milwaukee, Wis.) and methyl iodide (512.5 grams, 3.61 moles) in tetrahydrofuran (1000 ml) was cooled at 0° C. To this solution was added potassium tertiary butoxide (202.63 grams, 1.81 moles) portion-wise with stirring. During the process of addition, the temperature of the reaction mixture was kept at 0° C. to avoid exothermic reaction. White precipitate developed, and the mixture became very viscous. The cooling bath was removed, and the resulting mixture was heated at reflux for 7 hours. The mixture was stirred at room temperature for 15 hours, and then poured into methanol. The mixture was concentrated in vacuo and the residue was dissolved in water. The aqueous layer was extracted with diethyl ether and the extracts were combined. The residue (68 grams orange oil) was chromatographed (silica gel, elution by 10% ethyl acetate in hexanes) to give 24.25 grams (35%) of 6-fluoro-3,3-dimethyl-2,3-dihydro-4H-chromen-4-one as a yellow solid.

MS (ES) m/z: 195.1 (M+H).

H-NMR (δ, CDCl$_3$): 1.21 (6H, s), 4.14 (2H, s), 6.94 (1H, dd, J=4.2, 9.00 Hz), 7.15-7.23 (1H, m), 7.54 (1H, dd, J=3.21, 9.00 Hz).

Further elution gave 5 grams of 6-fluoro-3-[3-(5-fluoro-2-methoxyphenyl)-2,2-dimethyl-3-oxopropyl]-3-methyl-2,3-dihydro-4H-chromen-4-one as a white solid, recrystalized from methanol to give colorless prisms. The structure was determined by X ray analysis.

MS (ES) m/z: 389.1 (M+H).

H-NMR (δ, CDCl$_3$): 1.06 (3H, s), 1.13 (3H, s), 1.17 (3H, s), 2.06 (1H, d, J=11.1 Hz), 2.28 (1H, d, J=11.1 Hz), 3.65 (3H, s), 4.16 (1H, d, J=8.7 Hz), 4.38 (1H, d, J=8.7 Hz), 7.02-7.22 (4H, m), 7.44-7.50 (2H, m).

Example 2

Reaction of 6-fluoro-2,3-dihydro-4H-chromen-4-one with Methyl Iodide in the Presence of Potassium Tertiary Butoxide at −78° C.

Preparation of 6-fluoro-3,3-dimethyl-2,3-dihydro-4H-chromen-4-one, Compound 1

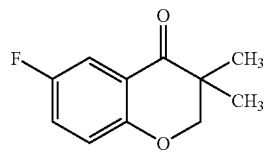

Potassium tertiary butoxide (104 grams, 0.93 mole) and tetrahydrofuran (1000 ml) were placed in a three necked round bottomed flask, equipped with a mechanical stirrer and an addition funnel, and the solution was cooled at −78° C. (bath temperature). A solution of 6-fluoro-2,3-dihydro-4H-chromen-4-one (38.8 grams, 0.235 mole) and iodomethane (118.6 grams, 52 ml, 0.835 mole) in tetrahydrofuran (300 ml) was added to the cooled solution. During the process of addition, the temperature of the reaction mixture was kept at −78° C. to avoid exothermic reaction. White precipitate developed, and the mixture became supernatant. Upon completing addition, TLC analysis indicated that most of the starting material was consumed. An additional amount (68.4 grams, 30 ml, 0.48 mole) of iodomethane was added all at once. The resulting white slurry was stirred and allowed to warm to room temperature over a period of 15 hours, and then filtered through a CELITE® cake. The filtrate was concentrated in vacuo to give 44.8 grams (98.3%) of 6-fluoro-3,3-dimethyl-2,3-dihydro-4H-chromen-4-one. Analytical HPLC (4.6×150 mm Prodigy™ ODS3 C18 column (Phenomenex, Torrance, Calif.) eluted with 10-100% acetonitrile in water containing 0.02% trifluoroacetic acid over 20 minutes): 97.5% at 14.84 minutes. Other physical properties of the product were the same as those described in Example 1.

Example 3

Reaction of 2,3-dihydro-4H-chromen-4-one with Methyl Iodide in the Presence of Potassium Tertiary Butoxide at −10-0° C.

Preparation of 3,3-dimethyl-2,3-dihydro-4H-chromen-4-one, Compound 3 and 3-[3-(2-methoxyphenyl)-2,2-dimethyl-3-oxopropyl]-3-methyl-2,3-dihydro-4H-chromen-4-one, Compound 4

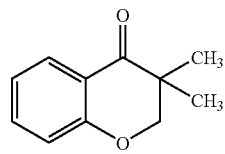

-continued

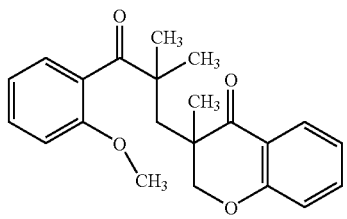

Compound 4

To a cooled (−10 to 0° C. bath temperature) solution of 2,3-dihydro-4H-chromen-4-one (8.0 grams, 0.054 mole) and iodomethane (22.8 grams, 10 ml, 0.16 mole) in anhydrous tetrahydrofuran (150 ml) was added portion-wise potassium tertiary butoxide (30 grams, 0.27 mole) under an argon atmosphere. During this process, the temperature was kept between −10 to 0° C. to avoid exothermic reaction. The cooling bath was removed, and the resulting mixture was warmed to room temperature. The mixture was heated at 60° C. for 4 hours, heated at reflux for 1 hour, and cooled to room temperature. Additional iodomethane (16 grams, 7 ml, 0.11 mole) was added, and heating was repeated at 60° C. for 4 hours and at reflux for 1 hour. The cooled solution was poured into a mixture of diethyl ether and water. The organic layer was separated, and the aqueous layer was extracted with diethyl ether. The combined extracts were washed with saturated sodium chloride aqueous solution, dried over sodium sulfate, and concentrated. The residue was chromatographed (silica gel, elution by methylene chloride) to give 5.62 grams (59.1%) of 3,3-dimethyl-2,3-dihydro-4H-chromen-4-one as a clear pale yellow oil.

MS (ES) m/z: 177.1 (M+H).

IR cm$^{-1}$: 0.1685, 1605, 1580, 1475.

H-NMR (δ, CDCl$_3$): 1.21 (6H, s), 4.13 (2H, s), 6.96 (1H, dd, J=0.6, 6.3 Hz), 7.03 (1H, ddd), 7.47 (1H, ddd) 7.91 (1H, dd, J=1.2, 7.5 Hz). Analysis for C$_{11}$H$_{12}$O$_2$: Calcd: C, 74.98; H, 6.86. Found: C, 74.70; H, 7.13.

Further elution by methylene chloride gave 2.8 grams (29.4%) of 3-[3-(2-methoxyphenyl)-2,2-dimethyl-3-oxopropyl]-3-methyl-2,3-dihydro-4H-chromen-4-one as a white solid.

MS (ES) m/z: 353.1 (M+H).

IR cm$^{-1}$: 1680, 1600, 1580, 1475.

H-NMR (δ, CDCl$_3$): 1.03 (3H, s), 1.12 (3H, s), 1.16 (3H, s), 2.12 (1H, d, J=11.1 Hz), 2.25 (1H, d, J=11.1 Hz), 3.64 (3H, s), 4.14 (1H, d, J=8.7 Hz), 4.39 (1H, d, J=8.7 Hz), 6.98-7.12 (5H, m), 7.32-7.42 (1H, m), 7.57-7.58 (1H, m), 7.74-7.77 (1H, m).

Analysis for C$_{22}$H$_{24}$O$_4$: Calcd: C, 74.98; H, 6.86. Found: C, 74.94; H, 7.08.

Example 4

Reaction of 2,3-dihydro-4H-chromen-4-one with Methyl Iodide in the Presence of Potassium Tertiary Butoxide at Low Temperature Preparation of 3,3-dimethyl-2,3-dihydro-4H-chromen-4-one, Compound 3

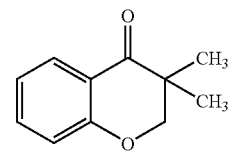

Compound 3

To a cooled (−78° C. bath temperature) solution of 2,3-dihydro-4H-chromen-4-one (25 grams, 0.169 mole) and iodomethane (120 grams, 53 ml, 0.945 mole) in anhydrous tetrahydrofuran (1000 ml) was added portion-wise potassium tertiary butoxide (94.5 grams, 0.945 mole) over a period of 1 hour under an argon atmosphere. During this process, the reaction temperature was kept at −78° C. to avoid exothermic reaction. The cooling bath was removed, and the resulting mixture was warmed to room temperature over a period of 4 hours. The white viscous mixture was heated at 60° C. (bath temperature) for 4 hours, cooled to room temperature, and stirred at room temperature for 15 hours. The resulting mixture was poured into a mixture of diethyl ether and water. The organic layer was separated, and the aqueous layer was extracted with diethyl ether. The combined extracts were washed with saturated sodium chloride aqueous solution, dried over sodium sulfate, and concentrated. The residue was chromatographed (silica gel, elution by methylene chloride) to give 30 grams (100%) of 3,3-dimethyl-2,3-dihydro-4H-chromen-4-one as a clear pale yellow oil. Physical properties of the product were the same as those described in Example 3.

The results of the preceding syntheses are summarized in Table 1, below.

TABLE 1

Syntheses Summary of Examples 1-4

| Starting compound | Iodomethane (mole equivalent) | Base (mole equivalent) | Initial Temperature (° C.) | Temperature (° C.) Time (hour) | Product Yield (%) |
|---|---|---|---|---|---|
| A | 10 | 5 | 0 | reflux (7) | 1 (35) + 2 |
| A | 5.5 | 4 | −78 | RT | 1 (98.3) |
| B | 5 | 5 | −10-0 | 60 (4 hours), reflux (1 hour) | 3 (59) + 4 (29.4) |
| B | 5.6 | 5.6 | −78 | RT, then 60 (4 hours) | 3 (100) |

It can be seen that the use of a metal alkoxide, for example, potassium tertiary butoxide, as a base, and a low reaction temperature can overcome the problems associated with ring opening, and give 3,3-dialkyl-4-chromanones, for example, 3,3-dimethyl-4-chromanones, in almost quantitative yields.

Although not wishing to be bound by a particular theory, it is believed that the dimer product is formed by a route wherein the carbanion resulting from the monoalkylation of the 3-position of the 4-chromanone starting material undergoes ring opening to form a vinylic intermediate, which is then attacked by a second monoalkylation carbanion species to produce the dimeric product, as shown for the reaction of 2,3-dihydro-4H-chromen-4-one and 6-fluoro-2,3-dihydro-4H-chromen-4-one in Scheme 2 below.

Scheme 2

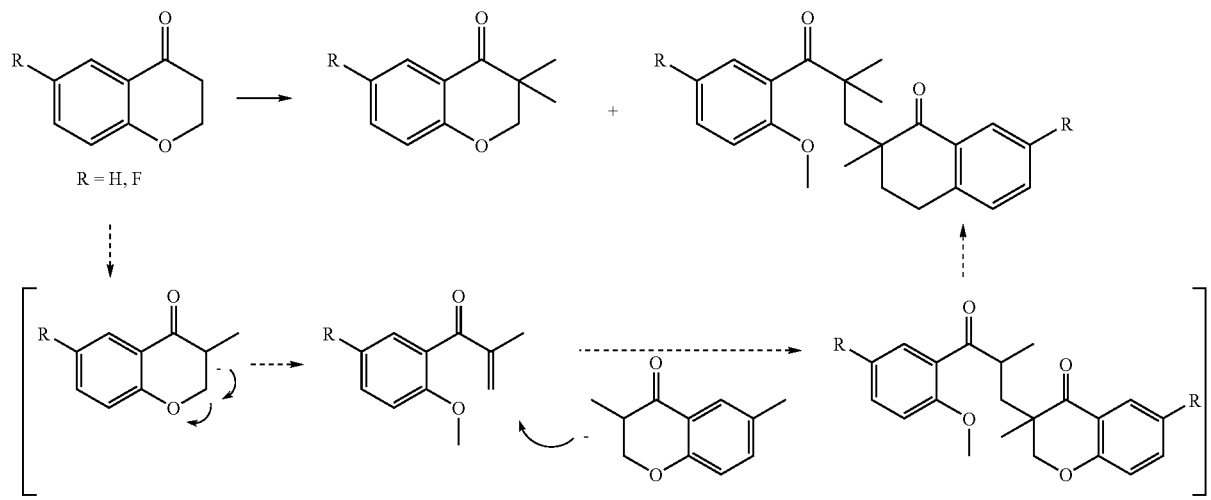

While not wishing to be bound by any particular theory, it is believed that performing the reaction at low temperatures suppresses the formation of the dimeric self-condensation product, allowing high yields of 3,3-dialkyl-4H-chromen-4-one products.

As those skilled in the art will appreciate, numerous changes and modifications may be made to the embodiments of the invention without departing from the spirit of the invention. It is intended that all such variations fall within the scope of the invention. It is intended that each of the patents, applications, and printed publications, including books, mentioned in this patent document be hereby incorporated by reference in their entirety.

What is claimed is:

1. A process for the preparation of a compound having the Formula I:

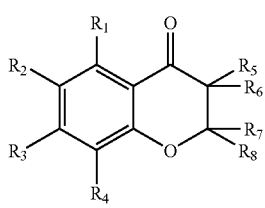

I wherein:

$R_1$, $R_2$, $R_3$, $R_4$, $R_7$ and $R_8$ are each, independently, selected from the group consisting of H, halogen, $C_{1-6}$ alkyl, $C_{1-6}$ alkoxy, $C_{1-3}$ perhaloalkyl and $C_{1-6}$ perhaloalkoxy;

wherein said $C_{1-6}$ alkyl and said $C_{1-6}$ alkoxy are each optionally substituted with up to five substitutents, independently, selected from the group consisting of halogen, phenyl, aryl, tertiary amines, optionally protected hydroxyl, optionally protected hydroxyl and optionally protected amino;

$R_5$ and $R_6$ are each independently $C_{1-12}$ alkyl or $C_{3-12}$ alkenyl, each of which is optionally substituted with up to five substitutents, independently, selected from the group consisting of halogen, phenyl, aryl, tertiary amines, optionally protected hydroxyl, and optionally protected amino;

comprising:

a) reacting a compound of Formula II:

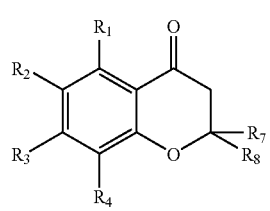

II with a $C_{1-12}$ alkyl halide or $C_{3-12}$ alkenyl halide in the presence of a metal alkoxide for a time and under conditions effective to form the compound of Formula I.

2. The process of claim 1 wherein the reaction of the compound of Formula II and the $C_{1-12}$ alkyl halide or $C_{3-12}$ alkenyl halide in the presence of the metal alkoxide is performed at a temperature that is less than about −20° C.

3. The process of claim 1 wherein the reaction of the compound of Formula II and the $C_{1-12}$ alkyl halide or $C_{3-12}$ alkenyl halide in the presence of the metal alkoxide is performed at a temperature that is less than about −40° C.

4. The process of claim 1 wherein the reaction of the compound of Formula II and the $C_{1-12}$ alkyl halide or $C_{3-12}$ alkenyl halide in the presence of the metal alkoxide is performed at a temperature that is less than about −60° C.

5. The process of claim 1 wherein the reaction of the compound of Formula II and the $C_{1-12}$ alkyl halide or $C_{3-12}$ alkenyl halide in the presence of the metal alkoxide is performed at a temperature that is less than about −70° C.

6. The process of claim 1 wherein the reaction of the compound of Formula II and the $C_{1-12}$ alkyl halide or $C_{3-12}$ alkenyl halide in the presence of the metal alkoxide is performed at a temperature that is about −78° C. or lower.

7. The process of claim 1 wherein the $C_{1-12}$ alkyl halide is a $C_{1-12}$ alkyl iodide.

8. The process of claim 1 wherein the $C_{1-12}$ alkyl halide is methyl iodide.

9. The process of claim 1 wherein the $C_{3-12}$ alkenyl halide is a $C_{3-12}$ alkenyl iodide.

10. The process of claim 1 wherein the $C_{3-12}$ alkenyl halide is alkenyl iodide.

11. The process of claim 1 wherein the metal alkoxide is a tertiary butoxide.

12. The process of claim 1 wherein the metal alkoxide is a potassium tert-butoxide.

13. The process of claim 1 wherein the compound of Formula II and the $C_{1-12}$ alkyl halide or $C_{3-12}$ alkenyl halide are reacted in the presence of potassium tert-butoxide at a temperature that is less than about −40° C.

14. The process of claim 1 wherein the compound of Formula II and the $C_{1-12}$ alkyl halide or $C_{3-12}$ alkenyl halide are reacted in the presence of potassium tert-butoxide at a temperature that is less than about −60° C.

15. The process of claim 1 wherein the compound of Formula II and the $C_{1-12}$ alkyl halide or $C_{3-12}$ alkenyl halide are reacted in the presence of potassium tert-butoxide at a temperature that is less than about −70° C.

16. The process of claim 1 wherein the compound of Formula II and the $C_{1-12}$ alkyl halide or $C_{3-12}$ alkenyl halide are reacted in the presence of potassium tert-butoxide at a temperature that is less than about −78° C.

17. The process of claim 1 wherein $R_2$ is H or halogen.

18. The process of claim 1 wherein $R_2$ is H or halogen, and $R_1$, $R_3$, $R_4$, and $R_8$ are each H.

19. The process of claim 1 wherein $R_2$ is H or halogen, $R_1$, $R_3$, $R_4$, $R_7$ and $R_8$ are each H, and $R_5$ and $R_6$ are each methyl.

20. The process of claim 1 wherein $R_2$ is H or fluorine, $R_1$, $R_3$, $R_4$, $R_7$ and $R_8$ are each H, and $R_5$ and $R_6$ are each methyl.

21. The process of claim 1 wherein the $C_{1-12}$ alkyl halide is methyl iodide, the metal alkoxide is potassium tert-butoxide, $R_2$ is H or fluorine, and $R_1$, $R_3$, $R_4$, $R_7$ and $R_8$ are each H.

22. The process of claim 20 wherein the compound of Formula II and the methyl iodide are reacted in the presence of potassium tert-butoxide at a temperature that is less than about −40° C.

23. The process of claim 20 wherein the compound of Formula II and the methyl iodide are reacted in the presence of potassium tert-butoxide at a temperature that is less than about −60° C.

24. The process of claim 20 wherein the compound of Formula II and the methyl iodide are reacted in the presence of potassium tert-butoxide at a temperature that is less than about −70° C.

25. The process of claim 20 wherein the compound of Formula II and the methyl iodide are reacted in the presence of potassium tert-butoxide at a temperature that is about −78° C. or lower.

26. The process of claim 1 wherein the reaction is performed in a solvent.

27. The process of claim 25 wherein the solvent is tetrahydrofuran.

28. The process of claim 1 wherein the molar ratio of $C_{1-12}$ alkyl halide to compound of Formula II is from about 2 to about 20.

29. The process of claim 1 wherein the molar ratio of $C_{1-12}$ alkyl halide to compound of Formula II is from about 2 to about 10.

30. The process of claim 1 wherein the molar ratio of $C_{1-12}$ alkyl halide to compound of Formula II is from about 2 to about 8.

31. The process of claim 1 wherein the molar ratio of $C_{1-12}$ alkyl halide to compound of Formula II is from about 4 to about 7.

32. The process of claim 1 wherein the molar ratio of $C_{1-12}$ alkyl halide to compound of Formula II is from about 5 to about 6.

33. The process of claim 1 wherein the molar ratio of metal alkoxide to compound of Formula II is from about 2 to about 10.

34. The process of claim 1 wherein the molar ratio of metal alkoxide to compound of Formula II is from about 3 to about 7.

35. The process of claim 1 wherein:
the reaction of the compound of Formula II and the $C_{1-12}$ alkyl halide in the presence of the metal alkoxide is performed at a temperature that is about −78° C. or lower;
the $C_{1-12}$ alkyl halide is methyl iodide;
the metal alkoxide is a potassium tert-butoxide;
$R_2$ is H or fluorine;
$R_1$, $R_3$, $R_4$, $R_7$ and $R_8$ are each H; and
$R_5$ and $R_6$ are each methyl.

36. The process of claim 34 wherein the solvent is tetrahydrofuran.

37. A process for the preparation of a compound of Formula III:

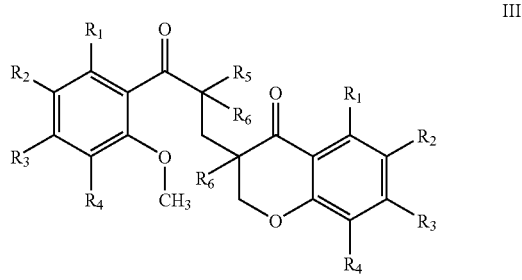

wherein:
$R_1$, $R_2$, $R_3$ and $R_4$ are each, independently, selected from the group consisting of H, halogen, $C_{1-6}$ alkyl, $C_{1-6}$ alkoxy, $C_{1-3}$ perhaloalkyl and $C_{1-6}$ perhaloalkoxy;
wherein said $C_{1-6}$ alkyl and said $C_{1-6}$ alkoxy are each optionally substituted with up to five substitutents, independently, selected from the group consisting of halogen, phenyl, aryl, tertiary amines, optionally protected hydroxyl, and optionally protected amino;
$R_5$ and $R_6$ are each independently $C_{1-12}$ alkyl or $C_{3-12}$ alkenyl halide, each of which is optionally substituted with up to five substitutents, independently, selected from the group consisting of halogen, phenyl, aryl, tertiary amines, optionally protected hydroxyl and optionally protected amino;

comprising:

a) reacting a compound of Formula II:

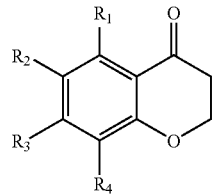

with a $C_{1-12}$ alkyl halide or $C_{3-12}$ alkenyl halide in the presence of a metal alkoxide for a time and under conditions effective to form the compound of Formula III.

38. The process of claim 37 wherein the reaction of the compound of Formula II and the $C_{1-12}$ alkyl halide or $C_{3-12}$ alkenyl halide in the presence of the metal alkoxide is performed at a temperature that is greater than about $-10°$ C.

39. The process of claim 37 wherein the reaction of the compound of Formula II and the $C_{1-12}$ alkyl halide or $C_{3-12}$ alkenyl halide in the presence of the metal alkoxide is performed at a temperature that is at about $-0°$ C. or greater.

40. The process of claim 37 wherein the reaction of the compound of Formula II and the $C_{1-12}$ alkyl halide or $C_{3-12}$ alkenyl halide in the presence of the metal alkoxide is performed at a temperature that at about $10°$ C. or greater.

41. The process of claim 37 wherein the reaction of the compound of Formula II and the $C_{1-12}$ alkyl halide or $C_{3-12}$ alkenyl halide in the presence of the metal alkoxide is performed at a temperature that is about $20°$ C. or greater.

42. The process of claim 37 wherein the $C_{1-12}$ alkyl halide is a $C_{1-12}$ alkyl iodide.

43. The process of claim 37 wherein the $C_{1-12}$ alkyl halide is methyl iodide.

44. The process of claim 37 wherein the $C_{3-12}$ alkenyl halide is a $C_{3-12}$ alkenyl iodide.

45. The process of claim 37 wherein the $C_{3-12}$ alkenyl halide is alkenyl iodide.

46. The process of claim 37 wherein the metal alkoxide is a tertiary butoxide.

47. The process of claim 37 wherein the metal alkoxide is a potassium tert-butoxide.

48. The process of claim 37 wherein the compound of Formula II and the $C_{1-12}$ alkyl halide are reacted in the presence of potassium tert-butoxide at a temperature that is about $0°$ C. or greater.

49. The process of claim 37 wherein $R_2$ is H or halogen.

50. The process of claim 37 wherein $R_2$ is H or halogen, and $R_1$, $R_3$ and $R_4$ are each H.

51. The process of claim 37 wherein $R_2$ is H or halogen, $R_1$, $R_3$ and $R_4$ are each H, and $R_5$ and $R_6$ are each methyl.

52. The process of claim 37 wherein $R_2$ is H or fluorine, $R_1$, $R_3$ and $R_4$ are each H, and $R_5$ and $R_6$ are each methyl.

53. The process of claim 37 wherein the $C_{1-12}$ alkyl halide is methyl iodide, the metal alkoxide is potassium tert-butoxide, $R_2$ is H or halogen, and $R_1$, $R_3$ and $R_4$ are each H.

54. The process of claim 53 wherein the compound of Formula II and the methyl iodide are reacted in the presence of potassium tert-butoxide at a temperature that is about $-0°$ C. or greater.

55. The process of claim 53 wherein the compound of Formula II and the methyl iodide are reacted in the presence of potassium tert-butoxide at a temperature that is about $10°$ C. or greater.

56. The process of claim 53 wherein the compound of Formula II and the methyl iodide are reacted in the presence of potassium tert-butoxide at a temperature that is about $20°$ C. or greater.

57. The process of claim 37 wherein the reaction is performed in a solvent.

58. The process of claim 57 wherein the solvent is tetrahydrofuran.

59. The process of claim 37 wherein the molar ratio of $C_{1-12}$ alkyl halide to compound of Formula II is from about 2 to about 20.

60. The process of claim 37 wherein the molar ratio of $C_{1-12}$ alkyl halide to compound of Formula II is from about 2 to about 10.

61. The process of claim 37 wherein the molar ratio of $C_{1-12}$ alkyl halide to compound of Formula II is from about 2 to about 8.

62. The process of claim 37 wherein the molar ratio of $C_{1-12}$ alkyl halide to compound of Formula II is from about 4 to about 7.

63. The process of claim 37 wherein the molar ratio of $C_{1-12}$ alkyl halide to compound of Formula II is from about 5 to about 6.

64. The process of claim 37 wherein the molar ratio of metal alkoxide to compound of Formula II is from about 2 to about 10.

65. The process of claim 37 wherein the molar ratio of metal alkoxide to compound of Formula II is from about 3 to about 7.

66. The process of claim 37 wherein:
the reaction of the compound of Formula II and the $C_{1-12}$ alkyl halide in the presence of the metal alkoxide is performed at a temperature that is about $0°$ C. or greater;
the $C_{1-12}$ alkyl halide is methyl iodide;
the metal alkoxide is a potassium tert-butoxide;
$R_2$ is H or fluorine;
$R_1$, $R_3$, $R_4$, $R_7$ and $R_8$ are each H; and
$R_5$ and $R_6$ are each methyl.

67. The process of claim 66 wherein the solvent is tetrahydrofuran.

68. A product of the process of claim 1.

69. A product of the process of claim 1 that contains less than about 10% of a product of Formula III:

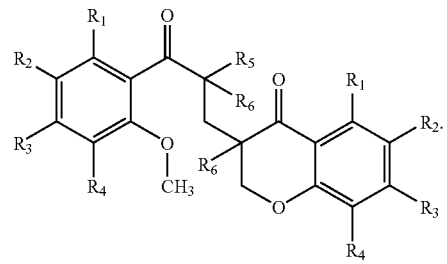

70. A product of claim 69 which contains less than about 5% said product of Formula.

71. A product of claim 69 which contains less than about 3% said product of Formula.

72. A product of claim 69 which contains less than about 1% said product of Formula.

73. A product of claim 69 which is substantially free of the product of Formula III.

74. A product of the process of claim 35.

75. A product of the process of claim 36.

76. A product of the process of claim 66.

77. A product of the process of claim 67.

* * * * *